US008835347B2

(12) United States Patent
Ruettinger et al.

(10) Patent No.: US 8,835,347 B2
(45) Date of Patent: Sep. 16, 2014

(54) ALKANE DEHYDROGENATION CATALYSTS

(75) Inventors: Wolfgang Ruettinger, E. Windsor, NJ (US); Michael Joseph Breen, Erie, PA (US); Richard Jacubinas, Bloomfield, NJ (US); Saeed Alerasool, Princeton Jct., NJ (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 12/479,289

(22) Filed: Jun. 5, 2009

(65) Prior Publication Data
US 2010/0312035 A1 Dec. 9, 2010

(51) Int. Cl.
*B01J 23/04* (2006.01)
*B01J 23/26* (2006.01)
*B01J 23/00* (2006.01)
*C07C 5/333* (2006.01)
*B01J 23/92* (2006.01)
*B29C 47/00* (2006.01)
*B01J 35/10* (2006.01)
*B01J 37/00* (2006.01)
*B01J 38/12* (2006.01)
*B01J 35/02* (2006.01)
*B01J 37/02* (2006.01)

(52) U.S. Cl.
CPC ............ *C07C 5/3332* (2013.01); *B01J 23/92* (2013.01); *B29C 47/00* (2013.01); *C07C 2521/04* (2013.01); *B01J 35/1019* (2013.01); *B01J 37/0009* (2013.01); *C07C 2523/26* (2013.01); *B01J 23/002* (2013.01); *B01J 2523/00* (2013.01); *B01J 23/26* (2013.01); *B29C 47/0033* (2013.01); *C07C 2523/04* (2013.01); *B29C 47/0019* (2013.01); *B29C 47/0023* (2013.01); *B29C 47/0011* (2013.01); *B01J 35/1014* (2013.01); *B01J 38/12* (2013.01); *B29C 47/003* (2013.01); *B01J 35/026* (2013.01); *B01J 37/0201* (2013.01)
USPC ........... 502/306; 502/305; 502/317; 502/319; 502/320

(58) Field of Classification Search
USPC .......................... 502/305, 306, 317, 319, 320
See application file for complete search history.

(56) References Cited

U.S. PATENT DOCUMENTS

| 2,943,067 | A | 6/1960 | Sieg |
| 2,945,823 | A | 7/1960 | Cornelius et al. |
| 2,956,030 | A | 10/1960 | Cornelius et al. |
| 3,285,985 | A | 11/1966 | Kline et al. |
| 3,725,495 | A | 4/1973 | Wrisberg et al. |
| 3,781,375 | A | 12/1973 | Shima et al. |
| 3,931,348 | A | 1/1976 | Taniguchi et al. |
| 4,128,590 | A | 12/1978 | Pollitzer et al. |
| 4,151,071 | A | 4/1979 | Myers |
| 4,379,134 | A | 4/1983 | Weber et al. |
| 4,420,649 | A | 12/1983 | Antos |
| 4,456,631 | A | 6/1984 | Crosbie et al. |
| 4,458,098 | A | 7/1984 | Antos |
| 4,886,928 | A | 12/1989 | Imai et al. |
| 5,308,822 | A | 5/1994 | Iezzi et al. |
| 5,723,707 | A | 3/1998 | Heyse et al. |
| 5,736,478 | A | 4/1998 | Cortright et al. |
| 5,759,946 | A | 6/1998 | Hoang et al. |
| 6,197,717 | B1 | 3/2001 | Alexander et al. |
| 6,239,325 | B1 | 5/2001 | Kishimoto et al. |
| 6,362,385 | B1 | 3/2002 | Iezzi et al. |
| 7,012,038 | B2 | 3/2006 | Alerasool et al. |
| 7,279,611 | B2 | 10/2007 | Alerasool et al. |
| 2003/0181323 | A1 | 9/2003 | Le Van Mao |
| 2003/0232720 | A1 | 12/2003 | Alerasool et al. |
| 2005/0075243 | A1 | 4/2005 | Fridman et al. |
| 2006/0149112 | A1 | 7/2006 | Rokicki et al. |

FOREIGN PATENT DOCUMENTS

| GB | 572251 | 9/1945 |
| WO | WO 03/106388 | * 12/2003 |

OTHER PUBLICATIONS

International Search Report PCT/US-3/18188 conducted on Oct. 22, 2003.

* cited by examiner

*Primary Examiner* — Elizabeth Wood
(74) *Attorney, Agent, or Firm* — Melanie L. Brown

(57) ABSTRACT

Disclosed are dehydrogenation catalyst composites and methods of making the dehydrogenation catalyst composites. The dehydrogenation catalyst composites contain alumina, lithium oxide, alkaline earth metal oxide, chromium oxide, and sodium oxide. Also disclosed are methods of dehydrogenating a dehydrogenatable hydrocarbon involving contacting the dehydrogenatable hydrocarbon with a dehydrogenation catalyst composite containing alumina, lithium oxide, alkaline earth metal oxide, chromium oxide, and sodium oxide to provide a dehydrogenated hydrocarbon, such as an olefin.

8 Claims, No Drawings

ALKANE DEHYDROGENATION CATALYSTS

TECHNICAL FIELD

The subject innovation generally relates to stable, long lasting dehydrogenation catalyst composites containing alumina, sodium, an alkaline earth metal, chromium, and optionally lithium and related methods and systems.

BACKGROUND

Lower olefins, such as propylene and isobutylene, can be produced by dehydrogenating lower alkanes. Various methods include industrially practiced dehydrogenation reactions using platinum catalysts, noble metal promoted zinc aluminate spinel catalysts, or chrome-alumina catalysts. However, these catalytic processes may suffer from two drawbacks. First, it is difficult to obtain high olefin yields due to equilibrium limitations of the dehydrogenation reaction. Second, the high temperatures typically required for these processes tend to degrade the catalyst.

One type of catalyst commonly used for dehydrogenating lower alkanes is an alumina supported chromia catalyst. Although this catalyst has a relatively high dehydrogenation activity, it may suffer from rapid coke formation during the dehydrogenation reaction. Consequently, frequent high temperature regeneration cycles are required. Due to the need for frequent regeneration, catalysts having a high degree of hydrothermal stability are desired in order to prevent frequent and costly catalyst replacement.

The rapid coke formation and frequent regeneration also necessitate the employment of cyclical processes, such as the Houdry process, when using chromia-alumina as a dehydrogenation catalyst. Cyclical processes make use of parallel reactors that contain a shallow bed of chromia-alumina catalyst. The feed is preheated through a fired heater before passing over the catalyst in the reactors. The hot product is cooled, compressed and sent to the product fractionation and recovery station. To facilitate continuous operation, the reactors are operated in a timed cycle. Each complete cycle typically consists of dehydrogenation, regeneration, reduction, and purge segments. A further requirement for continuous operation is the use of a parallel set of reactors, such as 3 to seven reactors. In an effort to circumvent equilibrium limitations, the reactors are operated at sub-atmospheric pressures during the dehydrogenation cycle (2 to 14 psia). Regeneration is performed with pre-heated air through a direct fire burner or with the exhaust of a gas turbine. Regeneration temperatures range from 550 degrees Celsius to 750 degrees Celsius.

Because of such severe operating conditions, dehydrogenation catalyst life is typically one to less than two years. Catalyst replacement is performed when conversion and selectivity fall below minimum levels required for the economic operation of the unit. For example, a dehydrogenation catalyst may have an initial conversion and selectivity values of 50-60% and 88-90%, respectively, while end-of-life conversion and selectivity values are typically 40-45% and 75-85%, respectively.

SUMMARY

The following presents a simplified summary of the innovation in order to provide a basic understanding of some aspects of the innovation. This summary is not an extensive overview of the innovation. It is intended to neither identify key or critical elements of the innovation nor delineate the scope of the innovation. Rather, the sole purpose of this summary is to present some concepts of the innovation in a simplified form as a prelude to the more detailed description that is presented hereinafter.

The subject innovation provides dehydrogenation catalyst composites that can exhibit one or more of high activity, high selectivity, robust hydrothermal stability, high yields, long catalyst life cycles, low deactivation rates, and high surface area retention. The high surface area retention is achievable even while operating at high temperatures. Furthermore, the dehydrogenation catalyst composites can be advantageously employed without supplemental hydrogen. The dehydrogenation catalyst composites enable the efficient manufacture of feedstocks used in the production of polyolefins such as polypropylene and gasoline additives such as MTBE.

One aspect of the innovation relates to a dehydrogenation catalyst composite containing alumina, lithium oxide, alkaline earth metal oxide, chromium oxide, and sodium oxide where the alkaline earth metal oxide and chromium oxide are uniformly distributed within dehydrogenation catalyst composite. The innovation also relates to methods of making the dehydrogenation catalyst composite.

Another aspect of the innovation relates to method of dehydrogenating a dehydrogenatable hydrocarbon involving contacting the dehydrogenatable hydrocarbon with a dehydrogenation catalyst composite containing alumina, optionally lithium oxide, alkaline earth metal oxide, chromium oxide, and sodium oxide to provide a dehydrogenated hydrocarbon, such as an olefin.

To the accomplishment of the foregoing and related ends, the innovation involves the features hereinafter fully described and particularly pointed out in the claims. The following description set forth in detail certain illustrative aspects and implementations of the innovation. These are indicative, however, of but a few of the various ways in which the principles of the innovation may be employed. Other objects, advantages and novel features of the innovation will become apparent from the following detailed description of the innovation when considered in conjunction with the drawings.

DETAILED DESCRIPTION

The high temperature stable dehydrogenation catalyst composite (e.g., support and catalyst) in accordance with one aspect of the subject innovation contains alumina, alkaline earth metal oxide, chromium oxide, sodium oxide, and optionally lithium oxide. Generally speaking, the dehydrogenation catalyst composite is made by mixing alumina and optionally a lithium compound and/or a sodium compound to form an alumina mixture, optionally heating to a first temperature, combining an alkaline earth metal compound with the alumina mixture, optionally heating to a second temperature, combining a chromium compound and optionally a sodium compound with the alumina mixture, and heating to a third temperature (in the event a first heat treatment and/or a second heat treatment are employed). Alternatively, the dehydrogenation catalyst composite is made by mixing alumina, optionally a lithium compound and/or a sodium compound, and an alkaline earth metal compound to form an alumina mixture, optionally heating to a first temperature, combining a chromium compound and a sodium compound (if the mixture does not contain a sodium compound) with the alumina mixture, and heating to a second temperature (in the event a first heat treatment is employed).

In one embodiment, alumina, optionally a lithium and/or a sodium compound, and optionally one or more additives are initially mixed together. Then the mixture is combined with an alkaline earth metal compound and optionally a sodium compound (if the mixture does not contain a sodium compound). The chromium compound is added at a time when the alkaline earth metal compound is not added. Alternatively, the mixture is combined with an alkaline earth metal compound, optionally dried and/or calcined, and then combined with a chromium compound and optionally a sodium compound. In another embodiment, alumina, optionally a lithium compound and/or a sodium compound, an alkaline earth metal compound, and optionally one or more additives are initially mixed together. The mixture is combined with a chromium compound and optionally a sodium compound. In yet another embodiment, alumina, at least one of a lithium compound, a sodium compound, an alkaline earth metal compound, and optionally one or more additives are initially mixed together, then a chromium compounded is added to the mixture. Then the mixture is combined with a lithium compound when the mixture does not contain the lithium compound, with an alkaline earth metal compound when the mixture does not contain the alkaline earth metal compound, and with a sodium compound when the mixture does not contain the sodium compound.

Any suitable alumina material can be used. Specific examples of alumina that can be used include aluminum oxyhydroxide, boehmite, diaspore, and transitional aluminas such as alpha-alumina, beta-alumina, gamma-alumina, delta-alumina, eta-alumina, kappa-alumina, theta-alumina, rho-alumina, and chi alumina, aluminum trihydroxide, such as gibbsite, bayerite, nordstrandite, and doyelite. Examples of commercially available material include those under the trade designation Pural® (such as 200, BT, NF, NG, SB, SBI, SCC, and SCF) and Catapal® (such as A, B, and C1) from Sasol and those under the trade designation Versal® (such as Versal B) from UOP, Inc.

The lithium compound can be converted to lithium oxide during heating. The lithium compound is a molecule containing at least one atom of lithium. General examples of lithium compounds include lithium salts, organolithium compounds, lithium, and lithium oxide. Specific examples of lithium compounds include lithium metal powder, lithium acetate, lithium amide, lithium borates, lithium carbonate, lithium formate, lithium halides such as lithium fluoride, lithium chloride, lithium bromide, and lithium iodide, lithium hydride, lithium hydroxide, lithium hypochlorite, lithium nitrate, lithium nitride, lithium phosphate, lithium silicate, lithium zirconate, lithium perchlorate, lithium peroxide, lithium metasilicate, lithium sulfate, lithium butyllithium, lithium methyllithium, lithium phenyllithium, and the like. While not wishing to be bound by any theory, it is believed that the subsequently formed lithium oxide stabilizes defect sites within the alumina.

The alkaline earth metal compound can be converted to alkaline earth metal oxide during heating. The alkaline earth metal compound is a molecule containing at least one atom of alkaline earth metal. Alkaline earth metals include beryllium, magnesium, calcium, strontium, barium, and radium.

General examples of alkaline earth metal compounds include alkaline earth metal salts, organoalkaline earth metal compounds, alkaline earth metals, and alkaline earth metal oxides. Examples of alkaline earth metal compounds include alkaline earth metal powder, alkaline earth metal acetate, alkaline earth metal amide, alkaline earth metal borates, alkaline earth metal carbonate, alkaline earth metal formate, alkaline earth metal halides such as alkaline earth metal fluoride, alkaline earth metal chloride, alkaline earth metal bromide, and alkaline earth metal iodide, alkaline earth metal hydride, alkaline earth metal hydroxide, alkaline earth metal hypochlorite, alkaline earth metal nitrate, alkaline earth metal nitride, alkaline earth metal phosphate, alkaline earth metal silicate, alkaline earth metal zirconate, alkaline earth metal perchlorate, alkaline earth metal peroxide, alkaline earth metal metasilicate, alkaline earth metal sulfate, alkaline earth metal monohydrogen orthophosphate, trialkaline earth metal orthophosphate, alkaline earth metal hypophosphate, alkaline earth metal pyrophosphate, alkaline earth metal sulfite, alkaline earth metal oxalate, alkaline earth metal citrate, alkaline earth metal methylate, alkaline earth metal propylate, alkaline earth metal pentylate, alkaline earth metal ethoxide, or the like.

Specific examples of alkaline earth metal compounds include barium metal powder, barium acetate, barium amide, barium borates, barium carbonate, barium formate, barium halides such as barium fluoride, barium chloride, barium bromide, and barium iodide, barium hydride, barium hydroxide, barium hypochlorite, barium nitrate, barium nitride, barium phosphate, barium silicate, barium zirconate, barium perchlorate, barium peroxide, barium metasilicate, barium sulfate, barium monohydrogen orthophosphate, barium orthophosphate, barium hypophosphate, barium pyrophosphate, barium sulfite, barium oxalate, barium citrate, barium methylate, barium propylate, barium pentylate, barium ethoxide, strontium metal powder, strontium acetate, strontium amide, strontium borates, strontium carbonate, strontium formate, strontium halides such as strontium fluoride, strontium chloride, strontium bromide, and strontium iodide, strontium hydride, strontium hydroxide, strontium hypochlorite, strontium nitrate, strontium nitride, strontium phosphate, strontium silicate, strontium zirconate, strontium perchlorate, strontium peroxide, strontium metasilicate, strontium sulfate, strontium monohydrogen orthophosphate, strontium orthophosphate, strontium hypophosphate, strontium pyrophosphate, strontium sulfite, strontium oxalate, strontium citrate, strontium methylate, strontium propylate, strontium pentylate, strontium ethoxide, calcium metal powder, calcium acetate, calcium amide, calcium borates, calcium carbonate, calcium formate, calcium halides such as calcium fluoride, calcium chloride, calcium bromide, and calcium iodide, calcium hydride, calcium hydroxide, calcium hypochlorite, calcium nitrate, calcium nitride, calcium phosphate, calcium silicate, calcium zirconate, calcium perchlorate, calcium peroxide, calcium metasilicate, calcium sulfate, calcium monohydrogen orthophosphate, calcium orthophosphate, calcium hypophosphate, calcium pyrophosphate, calcium sulfite, calcium oxalate, calcium citrate, calcium methylate, calcium propylate, calcium pentylate, calcium ethoxide, magnesium metal powder, magnesium acetate, magnesium amide, magnesium borates, magnesium carbonate, magnesium formate, magnesium halides such as magnesium fluoride, magnesium chloride, magnesium bromide, and magnesium iodide, magnesium hydride, magnesium hydroxide, magnesium hypochlorite, magnesium nitrate, magnesium nitride, magnesium phosphate, magnesium silicate, magnesium zirconate, magnesium perchlorate, magnesium peroxide, magnesium metasilicate, magnesium sulfate, magnesium monohydrogen orthophosphate, magnesium orthophosphate, magnesium hypophosphate, magnesium pyrophosphate, magnesium sulfite, magnesium oxalate, magnesium citrate, magnesium methylate, magnesium propylate, magnesium pentylate, magnesium ethoxide, or the like.

While not wishing to be bound by any theory, it is believed that the subsequently formed alkaline earth metal oxide stabilizes defect sites within the alumina.

The sodium compound is a molecule containing at least one atom of sodium. The sodium compound can be converted to sodium oxide during heating. General examples of sodium compounds include sodium salts, sodium chromates, organosodium compounds, and sodium oxide. Specific examples of sodium compounds include sodium oxide, sodium fluoride, sodium chloride, sodium bromide, sodium iodide, sodium chromate, sodium dichromate, sodium acetate, sodium bicarbonate, sodium carbonate, sodium formate, sodium hydroxide, sodium metasilicate, sodium nitrate, sodium nitrite, sodium phosphate, sodium sulfate, sodium sulfite, and the like.

The alumina and lithium and sodium compound can be mixed to uniformly distribute the lithium compound and sodium compound in the alumina. In one embodiment, the mixture contains about 85% or more and about 99.9% or less of alumina and about 15% or less of the lithium compound and/or sodium compound (all % s by dry weight). In another embodiment, the mixture contains about 90% or more and about 99.5% or less of alumina and about 10% or less of the lithium and/or sodium compound. In yet another embodiment, the mixture contains about 95% or more and about 99% or less of alumina and about 5% or less of the lithium compound and/or the sodium compound. Alternatively, if the lithium compound and/or sodium compounds are not initially mixed with alumina, then the mixture contains about 85% or more and about 100% or less of alumina.

The alumina, lithium compound, sodium compound and alkaline earth metal compound can be mixed to uniformly distribute the lithium compound, sodium compound and alkaline earth metal compound in the alumina. In one embodiment, the mixture contains about 55% or more and about 99.8% or less of alumina, about 15% or less of the lithium and/or sodium compounds, and about 0.1% or more and about 30% or less of the alkaline earth metal compound (all % s by dry weight). In another embodiment, the mixture contains about 65% or more and about 99% or less of alumina, about 10% or less of the lithium and/or sodium compounds, and about 0.5% or more and about 25% or less of the alkaline earth metal compound. In yet another embodiment, the mixture contains about 75% or more and about 98% or less of alumina, about 5% or less of the lithium and/or sodium compounds, and about 1% or more and about 20% or less of the alkaline earth metal compound.

The alumina mixture, whether or not the lithium compound, sodium compound and/or the alkaline earth metal compound are present, can contain optional additives such as an extrusion agent, a rheology control agent such as Methocel®, binder, surface active agents, an acid, a base, clay, supplemental support materials such as silica, titania, zirconia, zinc oxide, boria, and the like. However, in one embodiment, supplemental support materials such as silica, titania, zirconia, zinc oxide, and boria are not added to the alumina mixture, and thus are not contained in the resultant catalyst composite, except in small or trace amounts.

The alumina mixture can be mixed well in a high shear mixer with water until a rather stiff dough is obtained. This dough can be extruded and/or formed into any suitable shape including cylinders, cubes, stars, tri-lobes, quadra-lobes, pellets, pills, or spheres by suitable mechanical means. In one embodiment, mixing is conducted in a high intensity environment, such as that supplied by a Littleford Mixer available from Littleford Day, Inc., Florence, Ky. Mixing is conducted for a time sufficient so that a fine uniform mix results.

After mixing, the alumina mixture can be formed or extruded into a suitable shape. The shape substantially corresponds to the shape of the resultant catalyst support. In one embodiment, the alumina mixture is extruded in a continuous manner over a broad range of diameters and shapes. Examples of forming or extrusion machines include extrusion molding machines, single screw extruders, twin screw extruders, coextruders, pin extruders, linear extruders, and monofilament extruders.

The alumina mixture can be then optionally formed into any desired shape. Examples of forming machines include molding machines, tableting machines, rolling granulators, marumarizers, and pelletors. The shape of the formed alumina mixture includes spheres, tablets, cylinders, stars, tri-lobes, quadra-lobes, pellets, pills, granules, honeycombs, and cubes. The shapes, generally referred to as "particulate," may have any suitable size. However, in a one embodiment, the sizes of the shapes are substantially uniform. The shaped material has its components (the alumina mixture and optionally lithium and/or sodium compound) mixed therein. In another embodiment, the shaped material has its components uniformly mixed therein.

After forming the material into a desired shape, the alumina mixture can be optionally dried to remove any remaining liquid (and typically to remove remaining water). Drying is conducted in a desiccator, under a vacuum (reduced pressure), and/or elevated temperature (baking) for a sufficient period of time to remove any remaining liquid from the shaped material.

The manner in which the shaped alumina mixture is dried is not critical. In one embodiment, the dried alumina mixture contains less than about 3% by weight free moisture. In another embodiment, the dried alumina mixture contains less than about 1% by weight free moisture.

In one embodiment, drying involves at least one of maintaining an elevated temperature (above about 35 degrees Celsius) overnight, desiccation overnight, and under a vacuum overnight. When employing elevated temperatures, in one embodiment, the shaped alumina mixture is heated from about 35 degrees Celsius to about 150 degrees Celsius for a time from about 5 seconds to about 6 hours.

The alumina mixture can be subjected to an optional heat treatment. If this heat treatment is performed, then it is a first heat treatment. The alumina mixture can be heated in an oxygen containing atmosphere such as air or water vapor. If alumina is combined with the lithium compound and/or alkaline earth metal compound, and optionally any additives in a water mixture, the shaped mixture may be optionally dried before heating. In one embodiment, the heat treatment involves heating at a temperature of about 500 degrees Celsius or more and about 1,100 degrees Celsius or less for about 1 minute or more and about 300 minutes or less. In another embodiment, the heat treatment involves heating at a temperature of about 600 degrees Celsius or more and about 1000 degrees Celsius or less for about 5 minutes or more and about 200 minutes or less. In yet another embodiment, the heat treatment involves heating at a temperature of about 650 degrees Celsius or more and about 950 degrees Celsius or less for about 10 minutes or more and about 150 minutes or less.

Although not critical to the innovation, if heat treated the alumina mixture has a surface area sufficient to facilitate incorporation of an alkaline earth metal component and/or a chromium compound thereon/therein. In one embodiment, the heat treated alumina mixture has a surface area of about 50 $m^2/g$ or more and about 400 $m^2/g$ or less. In another embodiment, the heat treated alumina mixture has a surface area of about 75 $m^2/g$ or more and about 300 $m^2/g$ or less. The heat treated alumina mixture, whether or not the lithium compound, the sodium compound and/or the alkaline earth metal component are present, can have a porous structure throughout the shaped mixture. The porous nature of the alumina mixture facilitates incorporation of the lithium compound (if not already present), alkaline earth metal compound (if not already present), chromium compound, sodium compound (if not already present), and additional additives therein during subsequent processing.

The incorporation of the optional lithium compound (if not already present), alkaline earth metal compound (if not already present), chromium compound, sodium compound (if not already present), and/or additional additives into the alumina mixture can occur throughout the alumina mixture. Unlike many catalyst composites where the catalytic metal is incorporated on the outer edges of a support, the alkaline earth metal compound and/or chromium compound are incorporated across the cross-sectional area of the resultant catalyst composite. That is, the alkaline earth metal compound and/or chromium compound can penetrate and can be present throughout the alumina mixture. In one embodiment, the alkaline earth metal compound and/or chromium compound are incorporated uniformly within the alumina mixture. The term uniformly is defined below.

An alkaline earth metal compound can be mixed with the heat treated alumina mixture.

A chromium compound can be mixed with the heat treated alumina mixture. If the alumina mixture does not contain a lithium compound and/or a sodium compound, then the lithium compound and/or sodium compound can be included with the chromium compound. The chromium compound is a molecule containing at least one atom of chromium. The chromium compound can be converted to chromium oxide during heating (one or more of chromium (III) oxide and chromium (VI) oxide). General examples of chromium compounds include chromium, chromium salts, chromates, chromic acid, and chromium oxides. Specific examples of chromium compounds include chromium, sodium chromate, sodium dichromate, potassium chromate, potassium dichromate, ammonium dichromate, chromic acid, chromic chloride, chromic acetylacetonate, chromic potassium sulfate, chromium (III) oxide, chromium (VI) oxide, chromyl chloride, lead chromate, chromium nitride, chromium nitrate, chromium fluoride, and the like. It is noted that the chromium compound is not or does not contain an alkaline earth chromate such as barium chromate.

A sodium compound can be mixed with the heat treated alumina mixture. The sodium compound is a molecule which described previously in this document.

The alumina mixture, lithium compound (if not in the alumina mixture), and/or sodium compound (if not in the alumina mixture) and/or either of the alkaline earth metal compound (if not in the alumina mixture) or chromium compound can be combined with water (e.g., deionized water), and mixed so that the lithium compound (if not in the alumina mixture) and/or sodium compound (if not in the alumina mixture) and/or either the alkaline earth metal compound (if not in the alumina mixture) or chromium compound, are distributed around/in the alumina mixture (not just in the surface pores) due, in part, to the porous nature of the alumina mixture as a whole. The water is then removed, by at least one of reduced pressure and gentle heating.

After the alumina mixture, optional lithium compound (if not in the alumina mixture), alkaline earth metal compound (if not in the alumina mixture), chromium compound, and optional sodium compound are combined, optional drying is conducted to remove any remaining liquid (and typically to remove remaining water). Drying is conducted in a desiccator, under a vacuum (reduced pressure), and/or elevated temperature (baking) for a sufficient period of time to remove any remaining liquid. When employing elevated temperatures, in one embodiment, heating is conducted from about 35 degrees Celsius to about 150 degrees Celsius for a time from about 5 minutes to about 10 hours.

The manner in which the catalyst combination is dried is not critical. In one embodiment, the dried catalyst combination contains less than about 3% by weight free moisture. In another embodiment, the dried catalyst combination contains less than about 1% by weight free moisture.

In one embodiment, the heat treated alumina mixture is mixed with a lithium compound (if not already present), sodium compound (if not already present), and/or additional additives, and/or either the alkaline earth metal compound (if not already present) or chromium compound at one time. In another embodiment, the heat treated alumina mixture is mixed with an alkaline earth metal compound (if not already present) and the alumina mixture is subjected to drying and/or heat treatment. If the optional heat treatment is previously performed, then this is a second heat treatment. The heat treatment conditions can be the same as the above-mentioned heat treatment. Then the alumina mixture is mixed with a chromium compound, sodium compound, and/or additional additives.

Regardless of the specific method of making the catalyst or catalyst combination, the alkaline earth metal compound and the chromium compound are impregnated or combined separately and not at the same time. This is because proper dispersion of the alkaline earth metal and chromium within the catalyst is achieved when the alkaline earth metal compound and the chromium compound are added separately. While not wishing to be bound by any theory, it is believed that when more chromium is added than the alkaline earth metal (such as is generally the case as described elsewhere herein), there may be insufficient alkaline earth metal solubility when both the alkaline earth metal compound and the chromium compound are added together. Therefore, the alkaline earth metal compound and the chromium compound are added in different acts independently of each other.

It is noted that the alkaline earth metal compound can be added prior to the chromium compound, or the chromium compound can be added prior to the alkaline earth metal compound.

The catalyst combination can be subjected to a heat treatment. If the optional heat treatment(s) is previously performed, then this is a second or third heat treatment. The catalyst combination can be heated in an oxygen containing atmosphere such as air or water vapor. In one embodiment, the heat treatment involves heating at a temperature of about 500 degrees Celsius or more and about 900 degrees Celsius or less for about 1 minute or more and about 400 minutes or less. In another embodiment, the heat treatment involves heating at a temperature of about 550 degrees Celsius or more and about 800 degrees Celsius or less for about 5 minutes or more and about 300 minutes or less. In yet another embodiment, the heat treatment involves heating at a temperature of about 600 degrees Celsius or more and about 750 degrees Celsius or less for about 10 minutes or more and about 150 minutes or less. If a previous heat treatment (e.g., the first heat treatment and/or the second heat treatment) and this heat treatment are employed, the previous heat treatment can be higher than this heat treatment.

In one embodiment, the resultant catalyst composite contains about 30% or more and about 98% or less of alumina; about 1% or more and about 40% or less of chromium oxide; about 0.1% or more and about 20% or less of alkaline earth metal oxide; about 5% or less of lithium oxide; and about 0.01% or more and about 5% or less of sodium oxide (all % s by dry weight). In another embodiment, the catalyst composite contains about 32% or more and about 96% or less of alumina, about 2% or more and about 38% or less of chromium oxide, about 0.5% or more and about 18% or less of alkaline earth metal oxide, about 4% or less of lithium oxide, and about 0.05% or more and about 4% or less of sodium oxide. In yet another embodiment, the catalyst composite contains about 40% or more and about 95% or less of alumina, about 3% or more and about 35% or less of chromium oxide, about 1% or more and about 15% or less of alkaline earth metal oxide, about 3% or less of lithium oxide, and about 0.1% or more and about 3% or less of sodium oxide.

The resultant catalyst composite can contain one or more of lithium-aluminate phase (e.g., lithium-aluminate matrix), alkaline earth metal-aluminate phase (e.g., alkaline earth metal-aluminate matrix), alkaline earth metal-chromate phase (e.g., alkaline earth metal-chromate matrix). These phases or matrices can be porous. In one embodiment, the catalyst composite contains a lithium-aluminate phase and alkaline earth metal-aluminate phase with chromium oxide and sodium oxide uniformly incorporated in/on the phases. This distribution is obtained when the lithium compound and alkaline earth metal compound are initially mixed with alumina to form the alumina mixture, or when the lithium compound is initially mixed with alumina to form the alumina mixture, the alkaline earth metal compound is incorporated into the alumina mixture, and then the chromium compound and sodium compound are incorporated. In another embodiment, the catalyst composite contains a lithium-aluminate phase, alkaline earth metal-aluminate phase, and alkaline earth metal-chromate phase with sodium oxide uniformly incorporated in/on the phases. This distribution is obtained when the lithium compound, alkaline earth metal compound, and chromium compound are initially mixed with alumina to form the alumina mixture.

In yet another embodiment, the catalyst composite contains a porous alumina phase/matrix with lithium oxide, alkaline earth metal oxide, chromium oxide, and sodium oxide uniformly incorporated in/on the pores of the alumina phase/matrix. This distribution is obtained when the lithium compound and is added with the chromium compound and sodium compound to the alumina mixture (that does not contain a lithium compound and an alkaline earth metal compound), preceded or followed by addition of the alkaline earth metal compound. However, a lithium compound, a sodium compound and an alkaline earth metal compound can be initially mixed with alumina to form the alumina mixture and then the chromium compound added to the alumina mixture. In this embodiment, the catalyst composite contains a lithium-aluminate phase and alkaline earth metal-aluminate phase with chromium oxide uniformly incorporated in/on the lithium-aluminate phase and alkaline earth metal-aluminate phase.

The uniformity of chromium distribution or alkaline earth metal distribution throughout the catalyst composite can be assessed using a "chromium mapping" technique or an "alkaline earth metal mapping" technique. This can be performed through the use of a scanning electron microscope equipped with a wavelength dispersive x-ray detector. For example, a Hitachi S-3500 N microscope may be employed. As the detector scans across an individual catalyst composite pellet, it generates a number of x-ray counts which is proportional to the concentration of chromium or alkaline earth metal in a given position in the pellet. The number of counts recorded in the center of pellet is compared with that recorded from the outer edge locations.

In one embodiment, when the number of counts recorded in the center of pellet is within 30% of that recorded from the outer edge locations, the chromium or alkaline earth metal is uniformly distributed throughout the catalyst composite. In another embodiment, when the number of counts recorded in the center of pellet is within 20% of that recorded from the outer edge locations, the chromium or alkaline earth metal is uniformly distributed throughout the catalyst composite. In another embodiment, when the number of counts recorded in the center of pellet is within 10% of that recorded from the outer edge locations, the chromium or alkaline earth metal is uniformly distributed throughout the catalyst composite.

The catalyst composite has a ratio of chromium oxide to alkaline earth metal oxide that promotes stability and/or a low deactivation rate, and/or facilitates the catalytic dehydrogenation process. In one embodiment, the ratio of chromium oxide to alkaline earth metal oxide in the dehydrogenation catalyst composite is from about 1:1 to about 500:1 (on a weight basis). In another embodiment, the ratio of chromium oxide to alkaline earth metal oxide in the dehydrogenation catalyst composite is from about 2:1 to about 100:1. In another embodiment, the ratio of chromium oxide to alkaline earth metal oxide in the dehydrogenation catalyst composite is from about 5:1 to about 20:1.

The resultant catalyst composite optionally contains additives that promote stability and/or a low deactivation rate, and/or facilitate the catalytic dehydrogenation process. Examples of additives include surface active agents, binders, and the like. In one embodiment, the resultant catalyst composite contains about 0.01% or more and about 10% or less of an optional additive (all % s by weight). In another embodiment, the resultant catalyst composite contains about 0.05% or more and about 5% or less of an optional additive. These additives can be initially mixed with the alumina and lithium compound, and/or mixed with the lithium-alumina mixture along with the chromium compound.

In one embodiment, the catalyst composite of the subject innovation does not contain one or more of nickel, platinum, palladium, and zinc. In these embodiments, under some conditions one or more of nickel, platinum, palladium, and zinc may detrimentally effect the dehydrogenation reaction. In another embodiment, the catalyst composite of the subject innovation contains one or more of nickel, platinum, and palladium.

The resultant catalyst composite has a surface area sufficient to facilitate dehydrogenation reactions. In one embodiment, the catalyst composite has a surface area of about 30 $m^2/g$ or more and about 300 $m^2/g$ or less. In another embodiment, the catalyst composite has a surface area of about 50 $m^2/g$ or more and about 250 $m^2/g$ or less. In yet another embodiment, the catalyst composite has a surface area of about 60 $m^2/g$ or more and about 150 $m^2/g$ or less.

The catalyst composite has an enhanced stability to retain the surface area sufficient to facilitate dehydrogenation reactions. The enhanced stability to retain the surface area can be evaluated using accelerated aging tests (e.g., heat treatment at elevated temperatures with elevated humidity conditions). In one embodiment, conditions of the heat treatment are at 800 degrees Celsius for 96 hours with air/steam (6%/94%, 800 sccm). In another embodiment, conditions of the heat treatment are at 850 degrees Celsius for 24 hours with air/steam (6%/94%, 800 sccm). In yet another embodiment, conditions of the heat treatment are at 850 degrees Celsius for 72 h with air/steam (20%/80% 1000 SCCM).

The catalyst composite can retain a high surface area after the heat treatment. In one embodiment, the catalyst composite retains a surface area of about 40 $m^2/g$ or more and about 300 $m^2/g$ or less after the heat treatment. In another embodiment, the catalyst composite retains a surface area of about 45

$m^2/g$ or more and about 300 $m^2/g$ or less after the heat treatment. In yet another embodiment, the catalyst composite retains a surface area of about 50 $m^2/g$ or more and about 300 $m^2/g$ or less after the heat treatment. While not wishing to be bound by any theory, it is believed that the alkaline earth metal-aluminate phase/matrix and/or alkaline earth metal-chromate phase/matrix may contribute the enhanced stability to retain the surface area. The surface area is determined by the art recognized BET method using $N_2$ as the adsorbate. The surface area is measured on an Ankersmit Quantachrome Autosorb-6 apparatus, after degassing samples at 180 degrees Celsius to a pressure of 3.3 Pa (25 mTorr). Alternatively, equivalent conditions and instruments can be used to determine the BET surface area.

The catalyst composite of the subject innovation is contacted with feedstock under suitable conditions to facilitate a dehydrogenation reaction. For example propane is used as a feedstock to produce propylene and isobutane is used as a feedstock to produce isobutylene. General examples of feedstock materials (dehydrogenatable hydrocarbons) include aliphatic compounds containing about 2 or more and about 30 or less carbon atoms per molecule, alkylaromatic hydrocarbons where the alkyl group contains about 2 or more and about 6 or less carbon atoms, and naphthenes or alkyl-substituted naphthenes where the alkyl group contains about 2 or more and about 6 or less carbon atoms. Specific examples of dehydrogenatable hydrocarbons include ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, ethylbenzene, n-butylbenzene, 1,3,5-triethylbenzene, isopropylbenzene, isobutylbenzene, ethylnaphthalene, and the like.

Generally speaking, the feedstocks suitable for use with the subject innovation generally contain paraffinic hydrocarbons having about 2 or more and about 20 or less carbon atoms. In another embodiment, the feedstocks contain paraffinic hydrocarbons having about 3 or more and about 12 or less carbon atoms. In one embodiment, the feedstocks boil at a temperature of about 400 degrees Celsius or less at atmospheric pressure. In another embodiment, the feedstocks boil at a temperature of about 250 degrees Celsius or less at atmospheric pressure.

In one specific embodiment, a catalytic process is provided for dehydrogenating hydrocarbons for direct or eventual upgrade to ethers such as, but not limited to, MTBE, ETBE, and TAME. Feedstocks for use with the subject innovation and suitable for providing etherification feedstocks generally contain aliphatic or alicyclic hydrocarbons having about 3 or more and about 7 or less carbon atoms. Since most etherification processes convert iso-olefins to ethers, the feedstock to such processes may require isomerization prior to etherification. The subject innovation can effectively dehydrogenate isoparaffins as well as normal paraffins therefore providing the flexibility to incorporate the process upstream, downstream or concurrent with an isomerization step.

In another specific embodiment, a process is provided for dehydrogenating hydrocarbons for improving gasoline research and/or motor octane. An olefinic hydrocarbon boiling in the gasoline or naphtha boiling point temperature range has a higher research and motor octane than its paraffinic counterparts. At least a portion of such feedstocks generally contain paraffinic hydrocarbons having about 3 or more and about 12 or less carbon atoms and the paraffinic hydrocarbon can be normal, branched, or a combination thereof.

In yet another specific embodiment, a process is provided to dehydrogenate hydrocarbons for use as feed to a petroleum refinery alkylation process. Feedstocks suitable for dehydrogenation for providing alkylation unit feedstock typically contain paraffinic hydrocarbons having about 2 or more and about 6 or less carbon atoms. In another embodiment, the feedstocks for providing alkylation unit feedstock contain paraffinic hydrocarbons having about 3 or more and about 5 or less carbon atoms including about 4 carbon atoms. The paraffinic fraction of such feedstocks can be normal, branched, or a combination thereof.

In still yet another specific embodiment, a process is provided to dehydrogenate hydrocarbons for use as feed for commercial chemical manufacture. Feedstocks having about 3 or more and about 5 or less carbon atoms are dehydrogenated into olefinic feedstocks for the subsequent production of polyethylene, polypropylene, polybutylene, polyisobutylene, or other chemical compositions that are commonly sold in solid or liquid forms.

The feedstocks can be processed through the catalytic processes of the subject innovation neat or can be combined with recycled portions of the product stream from the dehydrogenation process. Similarly, combinations of the above-described feedstock embodiments can be directed to the catalytic processes of the subject innovation and the products subsequently fractionated to individual product pools. The catalytic processes of the subject innovation can also be operated in "blocked out" mode where only one feedstock is processed through the facility at any one time.

The dehydrogenation process of the subject innovation optionally begins with preheating a hydrocarbon feedstock. The feedstock can be preheated in feed/reactor effluent heat exchangers prior to entering a furnace or contacting other high temperature waste heat as a means for final preheating to a targeted catalytic reaction zone inlet temperature. Suitable final preheating means include, for example, waste heat from other refinery processes such as a fluid catalytic cracking unit, a fluidized or delayed coking unit, a catalytic hydrocracker, a crude distillation unit, a catalytic reforming unit, and/or hydrotreating units found in conventional petroleum refineries.

The reaction zone can include one or more fixed bed reactors containing the same or different catalysts, a moving bed reactor, or a fluidized bed reactor. The feedstock may be contacted with the catalyst bed in one or more of an upward, downward, or radial flow fashion. The reactants may be in the liquid phase, mixed liquid and vapor phase, or the vapor phase.

In embodiments where a fixed bed reactor is employed, a dehydrogenation reaction zone may contain one or at least two fixed bed reactors. Fixed bed reactors in accordance with the subject innovation can also contain a plurality of catalyst beds. The plurality of catalyst beds in a single fixed bed reactor can also contain the same or different catalysts.

Since dehydrogenation reactions are generally endothermic, interstage heating, consisting of heat transfer devices between fixed bed reactors or between catalyst beds in the same reactor shell, can be employed. Heat sources can include conventional process heaters such as one or more process furnaces or can include internally produced heat such as that produced from catalyst regeneration within a fluidized catalytic process. Heating requirements may also be met from heating sources available from other refinery process units.

The dehydrogenation reaction zone effluent is generally cooled and the effluent stream is directed to a separator device such as a stripper tower where light hydrocarbons and hydrogen formed during the reaction step can be removed and directed to more appropriate hydrocarbon pools. Where the process is performed in the presence of supplemental hydrogen or sufficient internally generated hydrogen is produced, a separate hydrogen separation step can be performed upstream of and prior to light hydrocarbon separation. Some of the recovered hydrogen can be recycled back to the process while some of the hydrogen can be purged to external systems such as plant or refinery fuel.

The stripper liquid effluent product is then generally conveyed to downstream processing facilities. The olefin product optionally can be directed to a polymerization facility or to an isomerization process for isomerization and thereafter directed to an ether facility for conversion, in the presence of an alkanol, to an ether. Where at least a portion of the olefin from the process of the subject innovation is iso-olefin, the stream can be sent directly to an ether facility or to a polymerization facility. Prior to direction to an ether facility, the product stream can be purified by removing unconverted paraffinic hydrocarbon from the product. This unconverted product can be recycled back to the reaction zone or further manipulated in other process units. The olefin product can be directed to an alkylation process for reaction with isoparaffin to form higher octane, lower volatility gasoline blending components. The olefin product can be directed to a chemical manufacture process for conversion to other commodity chemical products or process streams. Methods for integration of the process of the subject innovation with other conventional refinery or chemical plant processes or products are known to those skilled in the art.

The catalyst composite is used at a temperature to facilitate catalytic dehydrogenation processes. In one embodiment, the temperature during catalytic dehydrogenation is about 250 degrees Celsius or higher and about 750 degrees Celsius or lower. In another embodiment, the temperature during catalytic dehydrogenation is about 400 degrees Celsius or higher and about 650 degrees Celsius or lower. Reaction temperatures below these ranges can result in reduced paraffin conversion and lower olefin yield. Reaction temperatures above these ranges can result in reduced olefin selectivity and lower olefin yields.

The catalyst composite is used at a pressure to facilitate catalytic dehydrogenation processes. In one embodiment, the pressure during catalytic dehydrogenation is about 0 psia (vacuum pressure) or more and about 500 psia or less. In another embodiment, the pressure during catalytic dehydrogenation is about 2 psia or more and about 20 psia or less. In another embodiment, the pressure during catalytic dehydrogenation is about 20 psia or more and about 300 psia or less. Excessively high reaction pressures increase energy and equipment costs and provide diminishing marginal benefits. Excessively high hydrogen circulation rates can also influence reaction equilibrium and drive the reaction undesirably towards reduced paraffin conversion and lower olefin yield.

The catalyst composite is used at a weight hourly space velocity (WHSV) to facilitate catalytic dehydrogenation processes. In one embodiment, the WHSV is about 0.1 $hr^{-1}$ or more and about 100 $hr^{-1}$ or less. In another embodiment, the WHSV is about 0.5 $hr^{-1}$ or more and about 50 $hr^{-1}$ or less. Feed space velocities exceeding the levels described herein generally result in a decline in paraffin conversion which overwhelms any gain in olefin selectivity, thereby resulting in lower olefin yield. Feed space velocities short of the levels described herein are generally costly in terms of capital requirements.

The dehydrogenation catalyst composite and process of the subject innovation provides superior overall dehydrogenation properties including one or more of high selectivity, high activity, low deactivation rate, high yields, and the like. In one embodiment, the dehydrogenation catalyst composites of the subject innovation can achieve paraffin conversion levels of about 50% or more. In another embodiment, the dehydrogenation catalyst composites can achieve paraffin conversion levels of about 60% or more. In one embodiment, the dehydrogenation catalyst composites of the subject innovation can achieve olefin selectivity levels of about 85% or more. In another embodiment, the dehydrogenation catalyst composites can achieve olefin selectivity levels of about 92% or more. In one embodiment, the dehydrogenation catalyst composites of the subject innovation can achieve olefin yield levels of about 40% or more. In another embodiment, the dehydrogenation catalyst composites can achieve olefin yield levels of about 50% or more.

The dehydrogenation catalyst and process of the subject innovation provides the above-described levels of performance while resisting catalyst deactivation, thereby extending catalyst cycle life under dehydrogenation conditions. This is due, in part, to the relatively high hydrothermal stability possessed by the dehydrogenation catalyst composites. In one embodiment, the dehydrogenation catalyst composites of the subject innovation have olefin yield deactivation loss levels of about 5% or less over a period of 200 days. In another embodiment, the dehydrogenation catalyst composites have olefin yield deactivation loss levels of about 2% or less over a period of 200 days. In yet another embodiment, the dehydrogenation catalyst composites have olefin yield deactivation loss levels of about 1% or less over a period of 200 days.

In one embodiment, the dehydrogenation catalyst composites of the subject innovation can be employed in olefin production without a substantial loss of yield (less than 5%) for about 200 days or more. In another embodiment, the dehydrogenation catalyst composites can be employed in olefin production without a substantial loss of yield for about 250 days or more. In another embodiment, the dehydrogenation catalyst composites can be employed in olefin production without a substantial loss of yield for about 300 days or more. In one embodiment, end-of-life conversion and selectivity values are reached after about 2 or more years of use. In another embodiment, end-of-life conversion and selectivity values are reached after about 2.5 or more years of use.

General examples of dehydrogenated hydrocarbons that are catalytically made from the feedstock materials include olefin compounds containing about 2 or more and about 30 or less carbon atoms per molecule, alkenylaromatic hydrocarbons where the alkenyl group contains about 2 or more and about 6 or less carbon atoms, and naphthenes or alkenyl-substituted naphthenes where the alkenyl group contains about 2 or more and about 6 or less carbon atoms. Specific examples of dehydrogenated hydrocarbons include ethylene, propylene, butene, isobutylene, pentene, isopentene, hexene, 2-methylpentene, 3-methylpentene, 2,2-dimethylbutene, heptene, 2-methylhexene, 2,2,3-trimethylbutene, cyclopentene, cyclohexene, methylcyclopentene, ethylcyclopentene, n-propylcyclopentene, propylenylpentane, 1,3-dimethylcyclohexene, styrene, butenylbenzene, triethenylbenzene, methylstyrene, isobutenylbenzene, ethenyinaphthalene, and the like.

The following examples illustrate the subject innovation. Unless otherwise indicated in the following examples and elsewhere in the specification and claims, all parts and percentages are by weight, all temperatures are in degrees Centigrade, and pressure is at or near atmospheric pressure.

Example 1

Preparation of a Dehydrogenation Catalyst Composite

Alumina trihydrate (22680 grams) and lithium nitrate (218 grams) are loaded into a 2.6 cubic feet Littleford mixer, then blended for 5 minutes. Nitric acid (70 wt %, 1134 grams) and water (3630 grams) are mixed for 83 minutes. This blend is formed into cylindrical extrudates (⅛" diameter), dried at 150 degrees Celsius, and then calcined in air at 600 degrees Celsius for 1 hour.

A portion of the calcined extrudates (1200 grams) is impregnated to incipient wetness with an aqueous solution of barium acetate (64.2 grams), dried at 120 degrees Celsius, and then calcined in air at 800 degrees Celsius for 2 hours.

A portion of the Ba-containing calcined alumina extrudates (250 grams) is impregnated to incipient wetness with an aqueous solution of chromic acid (82.5 grams) and sodium dichromate (8.7 grams). The sample is dried and calcined in air at 750 degrees Celsius for 2 hours.

Example 2

Comparative Catalyst

A catalyst is prepared according to Example 1, except that the Ba impregnation step is omitted in the preparation.

Example 3

Dehydrogenation Testing

The catalyst of Example 1 is compared to a the catalyst prepared according to Example 2. Catalyst tests are performed in a fixed bed continuous flow reactor. The catalyst charge is 125 ml. The reactor tube is heated in a tube furnace to 565 degrees Celsius in flowing nitrogen. Once the desired temperature is achieved, a feed consisting of 100% isobutane is passed over the catalyst bed at a gas hourly superficial velocity (GHSV) of 530 hr$^{-1}$ at 0.33 atm. The entire product stream is analyzed on-line using sampling valves and an HP 5890 chromatograph (TCD)/HP 5971 mass selective detector. The results are summarized in Table 1.

TABLE 1

| Catalyst | Example 1 | Example 2 |
| --- | --- | --- |
| Days on stream | 14 | 14 |
| Isobutane conversion (%) | 55.2 | 53.0 |
| Selectivity to isobutylene (%) | 93.4 | 95.7 |
| Yield of isobutylene (%) | 51.5 | 50.6 |

Table 1 demonstrates that the catalyst of Example 1 possesses dehydrogenation performance equivalent to the catalyst prepared according to Example 2.

Example 4

Accelerated Aging Test

Catalyst samples are loaded into a 1.5" diameter quartz tube furnace, then heated to 800 degrees Celsius at a heating rate of 8 degrees Celsius/min. Catalysts are then treated with air/steam (6%/94%, 800 sccm) for 96 hours, and cooled to room temperature in dry air (50 sccm). BET surface area analysis is used to determine extent of aging. Higher surface area retention is indicative of increased hydrothermal stability.

After the heat treatment, the catalyst of Example 1 retains a surface area of 55 m$^2$/gram, while the catalyst from Example 2 shows a surface area of 36 m$^2$/gram. These results demonstrate the enhanced hydrothermal stability of the catalyst from Example 1.

Example 5

Preparation of a Dehydrogenation Catalyst Composite

Alumina trihydrate (2700.4 grams) is loaded into a 10 L Eirich mixer and a solution containing water (150.2 grams) and barium acetate (67.5 grams) is added to the mixer. A solution containing water (210.5 grams), nitric acid (132.0 grams), and lithium nitrate (25.9 grams) is added to the mixer. The blend is mixed for a total of 23 minutes. An additional 9.9 grams of water is added to the blend and the blend is mixed for one more minute. The blend is formed into cylindrical extrudates (⅛" diameter), dried at 90 degrees Celsius overnight, and then calcined at 800 degrees Celsius for 2 hours in air. The calcined extrudates are allowed to cool in the furnace without external cooling.

A portion of the Ba-containing calcined alumina extrudates (250 grams) are impregnated to incipient wetness with an aqueous solution of chromic acid (82.4 grams), sodium dichromate solution (12.4 grams, 69% sodium dichromate dihydrate), and water (58.8 grams). The sample is dried and calcined in air at 750 degrees Celsius for 2 hours. The impregnated extrudates are allowed to cool in the furnace without external cooling.

Example 6

Dehydrogenation Testing

The catalyst from Example 5 is compared to a commercially produced Cr$_2$O$_3$/Al$_2$O$_3$ dehydrogenation catalyst. Catalyst tests are performed in a fixed bed continuous flow reactor as stated in Example 3. The results are summarized in Table 2.

TABLE 2

| Catalyst | Example 5 | Example 2 |
| --- | --- | --- |
| Days on stream | 12 | 12 |
| Isobutane conversion (%) | 61.6 | 58.0 |
| Selectivity to isobutylene (%) | 95.3 | 95.7 |
| Yield of isobutylene (%) | 58.8 | 55.5 |

Table 2 demonstrates that the catalyst of Example 5 possesses improved dehydrogenation performance compared to the commercially produced dehydrogenation catalyst reference.

Example 7

Accelerated Aging Test

Catalyst samples are loaded into a 1.5" quartz tube furnace, then heated to 850 degrees Celsius at a heating rate of 8 degrees Celsius/min. Catalysts are then treated with air/steam (6%/94%, 800 sccm) for 24 hours, and cooled to room temperature in dry air (50 sccm). BET surface area analysis is used to determine extent of aging. Higher surface area retention is indicative of increased hydrothermal stability.

After the heat treatment, the catalyst of Example 5 retains a surface area of 51 m²/gram, while the catalyst from Example 2 shows a surface area of 21 m²/gram. These results demonstrate the enhanced hydrothermal stability of catalyst from Example 5.

Example 8

Alumina trihydrate (2700 grams) and barium nitrate (69.03 grams) are loaded into a mixer and the material is mixed for 2 minutes. A solution containing water (345.6 grams), nitric acid (132.0 grams), and lithium nitrate (25.9 grams) is added to the mixer. The blend is mixed 34 minutes. The blend is formed into cylindrical extrudates (⅛" diameter), dried overnight, and then calcined in air at 900 degrees Celsius for 2 hours. The calcined extrudates are allowed to cool in the furnace without external cooling.

A portion of the Ba-containing calcined alumina extrudates (250 grams) are impregnated to incipient wetness with an aqueous solution of chromic acid (81.9 grams), sodium dichromate (9.2 grams), and water (65.3 grams). The sample is dried and then calcined in air at 750 degrees Celsius. The impregnated extrudates are allowed to cool in the furnace without external cooling.

Example 9

Alumina trihydrate (2700 grams) and 69.03 grams of Barium nitrate are loaded into a mixer and the material is mixed for 2 minutes. A solution containing water (345.6 grams), nitric acid (132.0 grams), sodium nitrate (45.47 grams) and lithium nitrate (25.9 grams) is added to the mixer. The blend is mixed 26 minutes. The blend is formed into cylindrical extrudates (⅛" diameter), dried overnight and then calcined at 900 degrees Celsius for 2 hours in air. The calcined extrudates are allowed to cool in the furnace without external cooling.

A portion of the Ba-containing calcined alumina extrudates (250 grams) are impregnated to incipient wetness with an aqueous solution of chromic acid (77.16 grams) and water (76.5 grams). The sample is dried for 2 hours at 120 degrees Celsius, and then impregnated again with an solution of chromic acid (10.28 grams) and water (46.3 grams). The sample is dried and then calcined in air at 750 degrees Celsius. The impregnated extrudates are allowed to cool in the furnace without external cooling.

Example 10

Alumina trihydrate (2700 grams) and barium nitrate (69.03 grams) are loaded into a mixer and mixed for 2 minutes. A solution containing water (345.6 grams) and nitric acid (132.0 grams) is added to the mixer. The blend is mixed for 34 minutes. The blend is formed into cylindrical extrudates (⅛" diameter), dried overnight, and then calcined at 900 degrees Celsius for 2 hours in air. The calcined extrudates are allowed to cool in the furnace without external cooling.

A portion of the Ba-containing calcined alumina extrudates (250 grams) are impregnated to incipient wetness with an aqueous solution of chromic acid (81.9 grams), sodium dichromate (9.2 grams), and water (64.2 grams). The sample is dried for 2 hours and then calcined in air at 750 degrees Celsius. The impregnated extrudates are allowed to cool in the furnace without external cooling.

Example 11

Accelerated Aging Test 2

Catalyst samples are loaded into inconel tubes (0.5" o.d.) located in a 2" quartz tube which is mounted in a vertical tube furnace. The catalysts are heated to 850 degrees Celsius at a heating rate of 5 degrees Celsius/min. Catalysts are then treated with air/steam (20%/80%, 1000 sccm) for 72 hours, and cooled to room temperature in dry air/nitrogen (1/1) mixture (1000 sccm). BET surface area analysis is used to determine extent of aging. Higher surface area retention is indicative of increased hydrothermal stability.

After the heat treatment, the catalyst of Example 8 retains a surface area of 42.7 m²/gram, the catalyst of Example 9 retains a surface area of 37.7 m²/g, the catalyst of Example 10 retains a surface area of 42.0 m²/g while the catalyst from Example 2 shows a surface area of 19.3 m²/gram. These results demonstrate the enhanced hydrothermal stability of catalysts from Example 8, Example 9 and Example 10.

Example 11

Activity Test of Catalysts Examples 8, 9 and 10

The catalyst from Example 4 is compared to a commercially produced $Cr_2O_3/Al_2O_3$ dehydrogenation catalyst. Catalyst tests are performed in a fixed bed continuous flow reactor as stated in Example 3. The results are summarized in Table 3.

TABLE 3

| Catalyst | Ex. 8 | Ex. 9 | Ex. 10 | Ex. 2 |
|---|---|---|---|---|
| Days on stream | 11 | 11 | 11 | 11 |
| Isobutane conversion (%) | 61.0 | 60.1 | 62.4 | 59.5 |
| Selectivity to isobutylene (%) | 97.0 | 97.4 | 96.3 | 96.8 |
| Yield of isobutylene (%) | 59.0 | 58.5 | 60.1 | 57.6 |

Table 3 demonstrates that the catalysts of Example 8, Example 9 and Example 10 possess improved dehydrogenation performance compared to the commercially produced dehydrogenation catalyst reference.

The dehydrogenation of dehydrogenatable hydrocarbons is an important commercial process because of the high and diverse demand for dehydrogenated hydrocarbons for use in the manufacture of various chemical products such as detergents, plastics, synthetic rubbers, pharmaceutical products, high octane gasoline, perfumes, drying oils, ion-exchange resins, and various other products well known to those skilled in the art. One example of this demand is in the manufacture of high octane gasoline by using C3 and C4 mono-olefins to alkylate isobutane. Another example of this demand is in the area of dehydrogenation of normal paraffin hydrocarbons to produce normal mono-olefins having from about 3 to about 30 carbon atoms per molecule. These normal mono-olefins can, in turn, be utilized in the synthesis of a vast number of other chemical products. Regarding the use of products made by the dehydrogenation of alkylaromatic hydrocarbons, they find wide application in the petroleum, petrochemical, pharmaceutical, detergent, plastic, and other industries.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

What has been described above includes examples of the disclosed information. It is, of course, not possible to describe every conceivable combination of components or methodologies for purposes of describing the disclosed information, but one of ordinary skill in the art can recognize that many further combinations and permutations of the disclosed information are possible. Accordingly, the disclosed information is intended to embrace all such alterations, modifications and variations that fall within the spirit and scope of the appended claims. Furthermore, to the extent that the term "includes," "has," "involve," or variants thereof is used in either the detailed description or the claims, such term is intended to be inclusive in a manner similar to the term "comprising" as "comprising" is interpreted when employed as a transitional word in a claim.

What is claimed is:

1. A dehydrogenation catalyst composite comprising:
   from about 30% by weight to about 98% by weight of alumina;
   from about 1% by weight to about 40% by weight of chromium oxide, wherein the chromium oxide is derived from a chromium compound that is not or does not contain an alkaline earth chromate;
   from about 0.1% by weight to about 20% by weight of an alkaline earth metal oxide comprising at least one of barium oxide and strontium oxide;
   up to about 5% by weight of lithium oxide; and
   about 0.01% by weight to about 5% by weight of sodium oxide,
   wherein the chromium oxide and the at least one of barium oxide and strontium oxide are uniformly distributed throughout the dehydrogenation catalyst composite, and
   wherein the strontium oxide is derived from one or more of the group selected from strontium metal powder, strontium acetate, strontium amide, strontium borates, strontium carbonate, strontium format, strontium halides such as strontium fluoride, strontium chloride, strontium bromide, and strontium iodide, strontium hydride, strontium hydroxide, strontium hypochlorite, strontium nitrate, strontium nitride, strontium phosphate, strontium silicate, strontium zirconate, strontium perchlorate, strontium peroxide, strontium metasilicate, strontium sulfate, strontium monohydrogen orthophosphate, strontium orthophosphate, strontium hypophosphate, strontium pyrophosphate, strontium sulfite, strontium oxalate, strontium citrate, strontium methylate, strontium propylate, strontium pentylate, or strontium ethoxide.

2. The dehydrogenation catalyst composite of claim 1, wherein the alkaline earth metal oxide is barium oxide.

3. The dehydrogenation catalyst composite of claim 1, wherein the chromium oxide and the at least one of barium oxide and strontium oxide are incorporated into a porous matrix of alumina separately from each other.

4. The dehydrogenation catalyst composite of claim 1, wherein the dehydrogenation catalyst composite comprises a barium-aluminate phase.

5. The dehydrogenation catalyst composite of claim 2, wherein the dehydrogenation catalyst composite comprises
   from about 32% by weight to about 96% by weight of alumina,
   from about 2% by weight to about 38% by weight of chromium oxide,
   from about 0.5% by weight to about 18% by weight of barium oxide,
   up to about 4% by weight of lithium oxide, and
   from about 0.05% by weight to about 4% by weight of sodium oxide.

6. The dehydrogenation catalyst composite of claim 2 further comprising from about 0.01% by weight to about 10% by weight of an additive comprising at least one selected from the group consisting of an extrusion agent, a rheology control agent, a binder, a surface active agent, and a clay.

7. The dehydrogenation catalyst composite of claim 1, wherein the dehydrogenation catalyst composite has a surface area from about 40 $m^2$/g to about 250 $m^2$/g.

8. The dehydrogenation catalyst composite of claim 2, wherein the dehydrogenation catalyst composite has at least one shape selected from the group consisting of spheres, tablets, cylinders, stars, tri-lobes, quadra-lobes, pellets, pills, granules, honeycombs, and cubes.

* * * * *